United States Patent [19]

Duncan

[11] Patent Number: 5,301,669

[45] Date of Patent: Apr. 12, 1994

[54] SYSTEM AND METHOD FOR PREVENTING ATRIAL COMPETITION DURING SENSOR-DRIVEN OPERATION OF A DUAL-CHAMBER PACEMAKER

[75] Inventor: James L. Duncan, Alpharetta, Ga.

[73] Assignee: Siemens Pacesetter, Inc., Sylmar, Calif.

[21] Appl. No.: 979,084

[22] Filed: Nov. 19, 1992

Related U.S. Application Data

[62] Division of Ser. No. 740,554, Aug. 5, 1991.

[51] Int. Cl.$^5$ .......................................... A61N 1/368
[52] U.S. Cl. ..................................................... 607/9
[58] Field of Search ................... 128/419 PG

[56] References Cited

U.S. PATENT DOCUMENTS

| | | | |
|---|---|---|---|
| 4,554,921 | 11/1985 | Boute et al. | 128/419 PG |
| 4,624,260 | 11/1986 | Baker, Jr. et al. | 128/419 PG |
| 4,788,980 | 12/1988 | Mann et al. | 128/419 PG |
| 4,856,523 | 8/1989 | Sholder et al. | 128/419 PG |
| 4,890,617 | 1/1990 | Markowitz et al. | 128/419 PG |

Primary Examiner—William E. Kamm
Assistant Examiner—Kennedy J. Schaetzle
Attorney, Agent, or Firm—Bryant R. Gold; Malcolm J. Romano

[57] ABSTRACT

A system and method for preventing atrial competition during sensor-driven operation of a dual-chamber pacemaker includes means for sensing atrial activity during an atrial refractory period. Atrial competition is avoided by either: (1) generating an atrial competition prevention (ACP) interval upon the detection of any atrial activity during the relative refractory portion of an atrial refractory period, and preventing any atrial stimulation pulses from being generated for the duration of such ACP interval; or (2) shortening the atrial refractory period in the event that the sensor-driven rate of the pacemaker begins to approach a rate that might place atrial stimulation pulses near the end of the unshortened atrial refractory period. Further, the invention includes features that allow monitoring of the intrinsic atrial rate to determine if such is much greater than the sensor-driven rate, and, if so: (1) reducing the maximum tracking rate of the pacemaker, and/or (2) switching the operating mode of the pacemaker from a dual-chamber sensor-driven mode to an single-chamber sensor-driven mode.

10 Claims, 7 Drawing Sheets

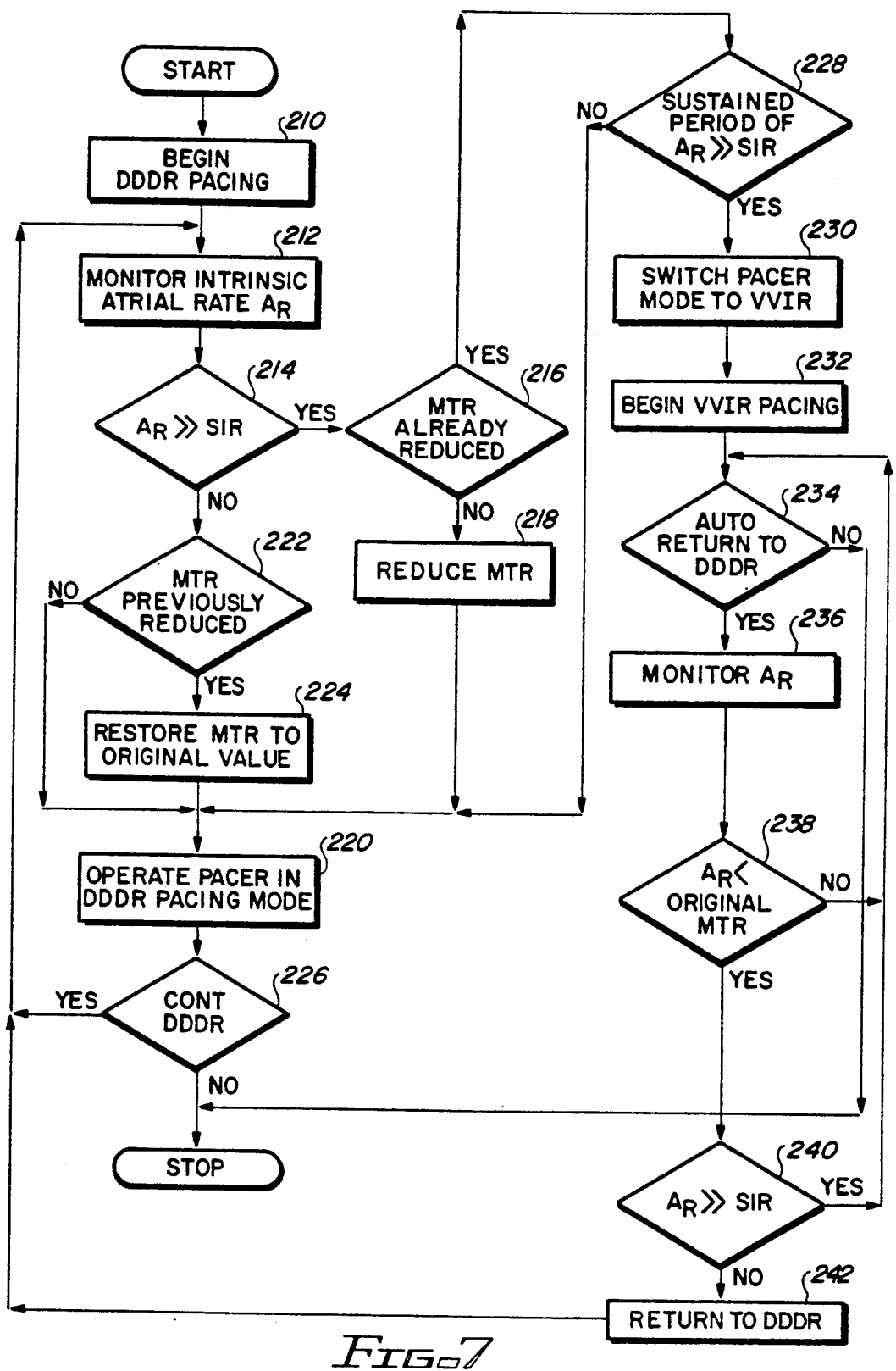

SYSTEM AND METHOD FOR PREVENTING ATRIAL COMPETITION DURING SENSOR-DRIVEN OPERATION OF A DUAL-CHAMBER PACEMAKER

This is a divisional of copending application Ser. No. 07/740,554 filed on Aug. 5, 1991.

BACKGROUND OF THE INVENTION

The present invention relates generally to programmable implantable pacemakers, and more particularly, to a system and method for preventing atrial competition in an implantable dual-chamber pacemaker programmed to operate in a sensor-driven mode, i.e., in a mode wherein a physiological sensor provides an indication of the rate at which the pacemaker should provide pacing pulses on demand.

A brief review of cardiac physiology and pacemaker technology will first be presented to help better understand the present invention and the terminology used herein.

The heart is a pump which pumps blood throughout the body. It consists of four chambers, two atria and two ventricles. In order to efficiently perform its function as a pump, the atrial muscles and ventricular muscles must contract in a proper sequence and timed relationship.

In a given cardiac cycle (corresponding to one "beat" of the heart), the two atria contract, forcing the blood therein into the ventricles. A short time later, the two ventricles contract, forcing the blood therein to the lungs (right ventricle) or through the body (left ventricle). Meanwhile, blood returning from the body fills up the right atrium and blood returning from the lungs fills up the left atrium, waiting for the next cycle to begin. A typical healthy adult heart may beat at a rate of 60-70 beats per minute (bpm) while at rest, and may increase its rate to 140-180 bpm when the adult is engaging in strenuous physical exercise, or undergoing other physiologic stress.

The healthy heart controls its own rhythm naturally from its sinal-atrial (S-A) node, located in the upper portions of the right atrium. The S-A node generates an electrical impulse at a rate commonly referred to as the "sinus" rate. This impulse is delivered to the atrial tissue when the atria are to contract; and, after a suitable delay (on the order of 120-180 milliseconds), is delivered to the ventricular tissue when the ventricles are to contract.

When the atria contract, a detectable electrical signal referred to as a P-wave is generated. When the ventricles contract, a detectable electrical signal referred to as an R-wave is generated. The R-wave is much larger than the P-wave, principally because the ventricular muscle tissue is much more massive than is the atrial muscle tissue. The atrial muscle tissue need only produce a contraction sufficient to move the blood a very short distance, from the respective atrium to its corresponding ventricle. The ventricular muscle tissue, on the other hand, must produce a contraction sufficient to push the blood over a long distance, e.g., through the complete circulatory system of the entire body.

Other electrical signals or waves are also detectable within a cardiac cycle, such as a Q-wave (which immediately precedes an R-wave), an S-wave (which immediately follows an R-wave), and a T-wave (which represents the repolarization of the ventricular muscle tissue).

A pacemaker is a medical device that provides electrical stimulation pulses to the appropriate chamber(s) of the heart (atria or ventricles) in the event the heart is unable to beat on its own, i.e., in the event either the S-A node fails to generate its own natural stimulation pulses at an appropriate sinus rate, or in the event such natural stimulation pulses are not delivered to the appropriate cardiac tissue. Most modern pacemakers accomplish this function by operating in a "demand" mode wherein stimulation pulses from the pacemaker are provided to the heart only when it is not beating on its own, as sensed by monitoring the appropriate chamber of the heart for the occurrence of a P-wave or an R-wave. If a P-wave or an R-wave is not sensed within a prescribed period of time (which period of time is most often referred to as the "escape interval"), then a stimulation pulse is generated at the conclusion of this prescribed period of time and delivered to the appropriate heart chamber via a pacemaker lead.

Further details associated with cardiac physiology and the operation of the heart as controlled or monitored by a pacemaker may be found, e.g., in U.S. Pat. No. 4,712,555 to Thornander et al.; U.S. Pat. No. 4,788,980 to Mann et al.; and/or U.S. Pat. No. 4,944,298 to Sholder. All three of these patents are incorporated herein by reference.

Pacemakers are typically both implantable within a patient and programmable, allowing their operation to be selectively controlled from a location external to the patient. Modern programmable pacemakers are generally of two types: (1) single-chamber pacemakers, and (2) dual-chamber pacemakers. The present invention relates to dual-chamber pacemakers, and more particularly to dual-chamber pacemakers operating in a rate-responsive mode.

In a single-chamber pacemaker, the pacemaker provides stimulation pulses to, and/or senses cardiac activity within, a single-chamber of the heart, e.g., either the right ventricle or the right atrium. In a dual-chamber pacemaker, the pacemaker provides stimulation pulses to, and/or senses cardiac activity within, two chambers of the heart, e.g., both the right ventricle and the right atrium. Typically, only the right atrium and/or the right ventricle is coupled to the pacemaker because of the relative ease with which a pacing lead can be transvenously inserted into either of these chambers. However, the left atrium and left ventricle can also be paced just as effectively providing that suitable electrical contact is made therewith.

In general, both single and dual-chamber pacemakers are classified by type according to a three or four letter code. In this code, the first letter identifies the chamber of the heart that is paced (i.e., that chamber where a stimulation pulse is delivered), with a "V" indicating the ventricle, an "A" indicating the atrium, and a "D" indicating both the atrium and ventricle. The second letter of the code identifies the chamber wherein cardiac activity is sensed, using the same letters to identify the atrium or ventricle or both, and wherein a "O" indicates no sensing takes place.

The third letter of the code identifies the action or response that is taken by the pacemaker. In general, three types of action or responses are recognized: (1) an Inhibiting ("I") response wherein a stimulation pulse is delivered to the designated chamber after a set period of time unless cardiac activity is sensed during that time, in which case the stimulation pulse is inhibited; (2) a Trigger ("T") response wherein a stimulation pulse is delivered to a prescribed chamber of the heart a prescribed period after a sensed event; (3) or a Dual ("D") response wherein both the Inhibiting mode and Trigger mode are evoked, e.g., inhibiting in one chamber of the heart and triggering in the other.

The fourth letter, when used, indicates whether the pacemaker is operating in a sensor-driven mode, i.e., in a mode wherein a physiological sensor is used to provide an indication of what the rate of the pacemaker should be. Such rate is often referred to as the sensor-indicated rate (SIR). The letter "R" is frequently used for the fourth letter to indicate use of such a sensor-driven mode.

Thus, for example, a DVI pacemaker is a pacer (note that throughout this application, the terms "pacemaker" and "pacer" may be used interchangeably) that paces in both chambers of the heart, but only senses in the ventricle, and that operates by inhibiting stimulation pulses when prior ventricular activity is sensed. Because it paces in two chambers, it is considered as a dual-chamber pacemaker. A VVI pacer, on the other hand, is a pacer that paces only in the ventricle and senses only in the ventricle. A VVIR pacer is a pacer that paces only in the ventricle at a rate determined by an appropriate physiological sensor, and senses only in the ventricle. Because only one chamber is involved, a VVI or VVIR pacer is classified as a single-chamber pacemaker.

Most dual-chamber pacemakers can be programmed to operate in any desired mode, including a single-chamber mode. Hence, e.g., a dual-chamber pacemaker may be programmed to operate in a DDD mode, i.e., a mode wherein the pacemaker paces and senses in both the atrium and the ventricle. If the dual-chamber pacemaker includes a physiological sensor, the dual-chamber pacemaker may be programmed to operate in a DDDR mode, i.e., a mode wherein the pacemaker provides stimulation pulses to both chambers of the heart on demand (i.e., only in the absence of natural atrial or ventricular activity in the respective chambers, as determined by sensing in both chambers) at a rate determined by the physiological sensor. The present invention addresses a problem that is primarily associated with a dual-chamber pacemaker operating in a DDDR mode.

One possible effect caused by operating a pacer in a DDD mode is atrial rate based pacing. In an atrial rate based pacemaker, the rate of the pacemaker is set by the heart's S-A node, and the ventricle is paced at a rate following the sensed atrial rate. Because the rate set by the S-A node represents the rate at which the heart should beat in order to meet the physiologic demands of the body, at least for a heart having a properly functioning S-A node, the rate maintained in the ventricle by such a pacemaker is truly physiologic. As indicated, a dual-chamber pacemaker, programmed to operate in the DDD mode, provides such physiologic pacing. That is, one of the functional states of DDD pacing, particularly applicable to patients having A-V block, is to sense P-waves in the atrium, i.e., to sense the rate set by the S-A node, and pace the ventricle at such sensed rate. Thus, as the physiologic rate increases, e.g., as the patient exercises and the P-wave rate increases, the pacemaker is able to track such increase and pace the ventricle accordingly.

Unfortunately, in a conventional DDD pacer, P-waves are tracked only up to a certain limit. If the P-waves occur too rapidly, they begin to fall in what is known as the atrial refractory period (ARP), the relevant portion of which is often referred to as the post ventricular atrial refractory period (PVARP) because it occurs after ventricular activity, whether such ventricular activity is paced or sensed. During the atrial refractory period, which is a prescribed time period set by the pacemaker logic circuits, P-waves are not sensed; or, if they are sensed, they are not considered as a P-wave, but are rather considered as noise. P-waves that occur during the PVARP thus have no effect on pacer timing. The PVARP is intended to provide a sufficient waiting period for the heart tissue to settle down or recover following a prior depolarization or contraction. (See, e.g., the previously cited '555 patent, and/or the '980 patent, for a more complete description of the timing intervals, and time periods, measured and/or generated by a typical pacemaker as it performs its function of providing stimulation pulses on demand.)

Thus, if the rate at which P-waves occur increases sufficiently to place a P-wave within the PVARP, such P-wave is not detected by a DDD pacer, and the occurrence of such P-wave has no effect on pacer timing. That is, the DDD pacer has no way of knowing that the P-wave occurred, so it waits until the next P-wave occurs, or until the pacemaker's applicable escape interval times out, whichever occurs first, before initiating the appropriate mechanism for issuing a ventricular stimulation pulse ("V-pulse"). Disadvantageously, for a situation where the intrinsic P-waves are gradually increasing, each being followed by a V-pulse, a point is reached (when the P-wave enters the PVARP) where the intrinsic P-wave is not sensed, resulting in an abrupt decrease in the ventricular paced rate.

In order to overcome this difficulty —of an abrupt decrease in the ventricular rate when tracking P-waves that enter the PVARP—it is known in the art to utilize a DDDR pacing mode. See Hanich et al., "Circumvention of Maximum Tracking Limitations with a Rate Modulated Dual-chamber Pacemaker," *PACE* 12:392-97 (Feb. 1989). Such DDDR pacing mode offers the advantage of providing a sensor-indicated back-up pacing rate after the intrinsic P-waves enter the PVARP. Thus, an abrupt decrease in the ventricular paced rate is avoided because the applicable escape interval in such a rate-responsive pacemaker, e.g., a DDDR pacemaker, is adjusted automatically as a function of the sensor-driven rate. Hence, as the intrinsic P-wave rate increases due to increased physiological demand brought about by, e.g., exercise, the applicable escape interval is shortened by the sensor-driven rate. Thus, even though a P-wave may enter the PVARP and not be sensed, the pacemaker will soon issue an atrial stimulation pulse, followed by a V-pulse, at a rate determined by the sensor-driven rate, thereby avoiding abrupt changes in ventricular paced rate.

Disadvantageously, however, once detection of the intrinsic P-wave is lost due to its falling within the PVARP, the resulting atrial stimulation pulse ("A-pulse") occurring at the sensor-indicated rate is in competition with the P-wave. Such atrial competition is undesirable because it may induce, in many patients, atrial arrhythmias. This is especially true in those instances where the patient's intrinsic atrial rate has increased due to increased physiological demand, as during physical exercise, because during such times the heart is experiencing higher myocardial oxygen demand and may be experiencing relative ischemia (inadequate flow of blood), both of which conditions may further promote the atrial arrhythmia.

An atrial arrhythmia, if it is short lived, is usually of no consequence. However, if it persists, it may result in an atrial tachycardia (a very rapid atrial rhythm) or fibrillation, both of which conditions pose serious health risks to the patient. Hence, what is needed is a method or technique for preventing atrial competition in a patient having a DDDR pacer, particularly when the DDDR pacer is sensing and tracking intrinsic P-waves that fall into the PVARP of the pacemaker.

Atrial competition also creates other problems. For example, atrial competition, by definition, applies an atrial stimulation pulse to atrial tissue as it is repolarizing (i.e., shortly after contraction). This action can significantly desensitize the atrial tissue to subsequent stimulation pulses, thereby making t difficult to achieve and maintain "capture" at those times when capture is needed to maintain a desired pacing rate. ("Capture" refers to the response of cardiac tissue to an applied stimulation pulse. When of sufficient energy, a stimulation pulse causes cardiac tissue to which it is applied to depolarize and contract; and the cardiac tissue is said to be "captured" by the stimulation pulse. When of insufficient energy, the cardiac tissue does not depolarize and contract; and the cardiac tissue does not respond, i.e., is not captured, by the stimulation pulse.) Thus, applying an A-pulse to the atrium in competition with a P-wave may make subsequent atrial capture difficult to achieve, as well as introduce atrial arrhythmias. Thus, what is needed is a system and method for operating a DDDR pacer wherein lack of capture is avoided, and atrial arrhythmias are prevented.

Further, should an atrial arrhythmia persist, there is a need in the art for a method or technique for quickly terminating such arrhythmia. However, before such terminating technique can be invoked, there is also a need for a reliable technique for distinguishing between a true atrial arrhythmia (a potentially dangerous cardiac condition) and a fast atrial rate (which may be a normal and needed response to a high oxygen demand condition, such as exercise).

Also, it is noted that as a practical matter atrial competition (i.e., the generating of an A-pulse in competition with an intrinsic P-wave) represents wasted energy of the limited energy resources of the implanted pacemaker. That is, the atrium, having just naturally depolarized and contracted, is not capable of depolarizing and contracting again until such time as the atrial cardiac tissue has repolarized. Thus, there is a further need to avoid atrial competition in order to preserve the limited energy resources of the pacemaker.

Advantageously, the dual-chamber, sensor-driven pacemaker described herein, including the method of operating such pacemaker, addresses the above and other needs.

SUMMARY OF THE INVENTION

The present invention provides a system and method for selectively preventing atrial competition during operation of the pacemaker in a dual-chamber, sensor-driven mode, e.g., the DDDR mode. This is accomplished by including within the DDDR pacemaker means for sensing atrial activity, e.g., a possible P-wave, during those times of the cardiac cycle, such as during a post ventricular atrial refractory period (PVARP), when such atrial activity would not be sensed by a conventional DDDR pacemaker. Means are also included within the pacemaker, responsive to sensing such atrial activity, for inhibiting any atrial stimulation pulse that would otherwise have been generated without affecting the time at which a ventricular stimulation pulse is generated. Hence, competition between the sensed atrial activity and an atrial stimulation pulse is prevented.

Advantageously, the present invention provides two alternate embodiments for avoiding atrial competition once atrial activity has been sensed: (1) generating an atrial competition prevention (ACP) interval upon the detection of any atrial activity during the relative refractory portion of an atrial refractory period, and then preventing any atrial stimulation pulses from being generated during the duration of such ACP interval; or (2) shortening the atrial refractory period in the event the sensor-driven rate of the pacemaker begins to approach a rate that might place atrial stimulation pulses near the end of the unshortened atrial refractory period.

One variation of the first embodiment (generating an ACP interval) inhibits the generation of the atrial stimulation pulse, but otherwise does not change the pacemaker timing, i.e., an atrial-ventricular delay (AVD) is initiated at the conclusion of the ventricular-atrial delay (VAD) that is set by the physiological sensor of the pacemaker. This sensor-controlled AVD is referred to herein as the sensor-indicated rate (SIR) VAD. Another variation of the first embodiment delays the generation of the atrial stimulation pulse until the conclusion of the ACP interval, thereby in effect extending the SIR VAD until the end of the ACP period.

One variation of the second embodiment (shortening the atrial refractory period) involves shortening the atrial refractory period a fixed amount. Another variation involves changing the atrial refractory period, within prescribed limits, as an inverse function of the sensor-indicated rate (SIR). Thus, if the SIR increases, the atrial refractory period is shortened. If the SIR decreases, the atrial refractory period is lengthened.

In accordance with one aspect of the invention, the atrial competition prevention means may be selectively programmed to be on or off. In the ACP interval embodiment, the ACP interval will typically have a value in the range of 250–350 milliseconds, although any suitable interval could be used. In the atrial refractory period shortening embodiment, the atrial refractory period will typically be shortened on the order of 50–100 milliseconds.

In accordance with another aspect of the invention, there is provided a means for distinguishing potentially dangerous atrial arrhythmias from normal fast atrial rates for a pacemaker operating in the DDDR mode, and means for terminating such atrial arrhythmias. The distinguishing means includes means for sensing the occurrence of a high intrinsic atrial rate and comparing such rate to the sensor-driven rate. A high intrinsic atrial rate in the absence of a corresponding high sensor-driven rate is presumed to be an atrial tachycardia condition—a potentially dangerous condition that needs to be terminated as quickly as possible. (Alternatively, such determination may indicate a malfunction of the pacemaker circuits and/or sensor responsible for generating the sensor-driven rate.) The terminating means, which operates only in response to detecting a high intrinsic atrial rate in the absence of a corresponding high sensor-driven rate includes means for automatically: (1) reducing the maximum tracking rate of the pacemaker; and/or (2) switching the operating mode of the pacemaker from a dual-chamber sensor-driven mode to a single-chamber sensor-driven mode, such as the VVIR mode. Advantageously, reducing the maximum tracking rate limits the rate at which the pacemaker can provide stimulation pulses. Switching the operating mode to a VVIR mode eliminates the possibility of atrial competition by eliminating any possibility of generating atrial stimulation pulses. Either of these responses, in turn, reduces the effects of the fast atrial rate condition.

Moreover, in the event the circuits/sensor responsible for generating the sensor-driven rate have somehow malfunctioned, neither of the responses to a detected disparity between the intrinsic atrial rate and the sensor-driven rate comprise responses that could worsen the situation until such time as the circuits/sensor can be replaced or repaired.

It is thus a feature of the invention to provide a dual-chamber pacemaker operating in a sensor-driven mode, and a method of operating such a pacemaker, that avoids atrial arrhythmias.

It is another feature of the invention to provide such a dual-chamber, sensor-driven pacemaker and method of operation that ensures that when an atrial stimulation pulse is provided, it captures the heart.

It is still another feature of the invention to provide a system and method for operating a dual-chamber, sensor-driven pacemaker that minimizes the likelihood of atrial competition between naturally occurring P-waves and atrial stimulation pulses which could induce an atrial arrhythmia.

It is a further feature of the invention, in accordance with one embodiment thereof, to provide such a system and method for operating a dual-chamber, sensor-driven pacemaker that detects atrial activity during the pacemaker's atrial refractory period and prevents any atrial stimulation pulses from being generated within a prescribed time interval thereafter, thereby minimizing atrial competition by assuring that there is always at least the prescribed time interval between sensed atrial activity and an atrial stimulation pulse.

It is an additional feature of the invention, in accordance with another embodiment thereof, to provide such a system and method for operating a dual-chamber, sensor-driven pacemaker that automatically shortens the pacemaker's atrial refractory period (ARP) whenever the sensor-driven rate approaches a rate that might place atrial stimulation pulses near the end of the time in the cardiac cycle when the original (unshortened) ARP terminates, thereby minimizing atrial competition by increasing the time period (after the ARP) during which atrial activity can be sensed, which atrial activity (if sensed after the ARP) inhibits the generation of an atrial stimulation pulse.

It is yet a further feature of the invention to provide a dual-chamber, sensor-driven pacemaker that includes means for detecting an atrial arrhythmia whenever there is a large disparity between a sensed atrial rate and the sensor-driven rate, and that further includes means for automatically dissociating the ventricular paced rate from the detected atrial rate, thereby perhaps reducing patient symptoms, and terminating such atrial arrhythmia once detected. In accordance with this feature, one embodiment of the invention causes the maximum tracking rate of the pacemaker to be reduced in response to a sensed atrial arrhythmia. Another embodiment causes the pacing mode of the pacemaker to automatically switch to a single-chamber sensor-driven mode, such as VVIR mode.

BRIEF DESCRIPTION OF THE DRAWINGS

The above and other aspects, features and advantages of the present invention will be more apparent from the following more particular description thereof, presented in conjunction with the following drawings wherein:

FIGS. 4, 5, 6 and 7 are flowchart diagrams illustrating the operation of the pacemaker of FIG. 1 in accordance with representative embodiments of the invention.

DETAILED DESCRIPTION OF THE INVENTION

Figure 1:
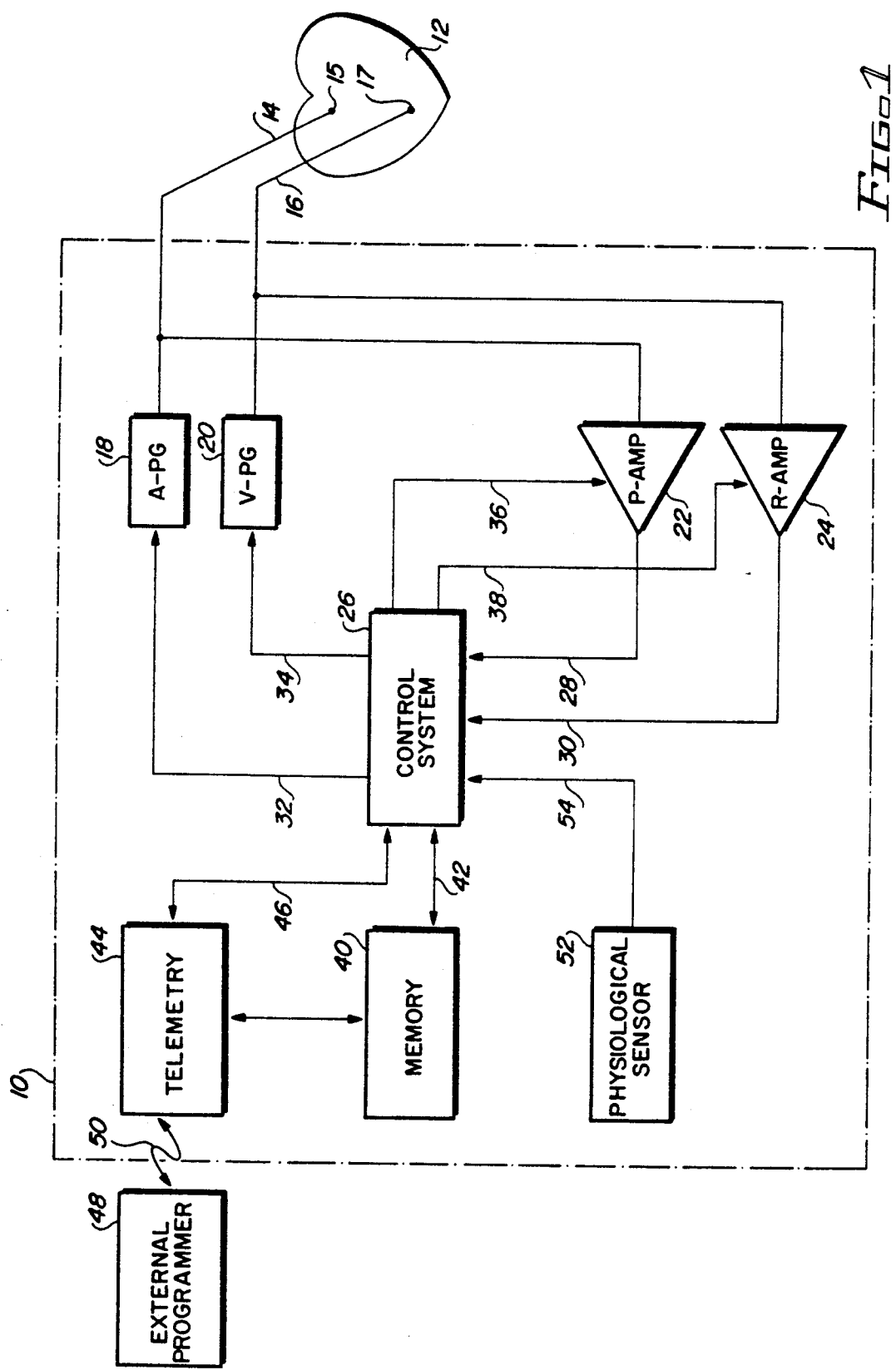
FIG. 1 is block diagram o a dual-chamber, programmable, rate-responsive pacemaker.

The following description is of the best mode presently contemplated for carrying out the invention. This description is not to be taken in a limiting sense, but is made merely for the purpose of describing the general principles of the invention. The scope of the invention should be determined with reference to the claims.

Before describing the present invention, it will be useful to describe the general framework of a programmable dual-chamber rate-responsive pacemaker, as such framework provides the basis within which the present invention is carried out. Accordingly, reference will first be made to FIGS. 1 and 2, where there is shown, respectively, a block diagram of a dual-chamber programmable pacemaker, and a block diagram of the control logic used within such a pacemaker. Once such framework has been described, the present invention will be described with reference to the timing diagrams of FIG. 3 and the flowchart diagrams of FIGS. 4, 5 and 6.

Referring first then to FIG. I, a simplified block diagram of a dual-chamber pacemaker 10 is illustrated. The pacemaker 10 is coupled to a heart 12 by way of leads 14 and 16, the lead 14 having an electrode 15 which is in contact with one of the atria of the heart, and the lead 16 having an electrode 17 which is in contact with one of the ventricles of the heart. The leads 14 and 16 carry stimulating pulses to the electrodes 15 and 17, respectively, from an atrial pulse generator (A-PG) 18 and a ventricular pulse generator (V-PG) 20, respectively. These stimulating pulses may be referred to herein as the "A-pulse" or the "V-pulse".

Further, electrical signals from the atria are carried from the electrode 15, through the lead 14, to the input terminal of an atrial sense amplifier (P-AMP) 22. Electrical signals from the ventricles are carried from the electrode 17, through the lead 16, to the input terminal of a ventricular sense amplifier (R-AMP) 24.

Controlling the dual-chamber pacer 10 is a control system 26. The control system 26 receives the output signals from the atrial sense amplifier 22 over a signal line 28. Similarly, the control system 26 receives the output signals from the ventricular sense amplifier 24 over a signal line 30. These output signals are generated each time that a P-wave or an R-wave is sensed within the heart 12.

The control system 26 also generates trigger signals which are sent to the atrial pulse generator 18 and the ventricular pulse generator 20 over two signal lines 32 and 34, respectively. These trigger signals are generated each time that a stimulation pulse is to be generated by the respective pulse generator 18 or 20.

During the time that either an A-pulse or V-pulse is being delivered to the heart, the corresponding sense amplifier, P-AMP 22 or R-AMP 24, is typically disabled by way of a blanking signal presented to these sense amplifiers from the control system over signal lines 36 and 38, respectively. This blanking action prevents the sense amplifiers 22 and 24 from becoming saturated from the relatively large stimulation pulses which are present at their input terminals during this time. This blanking action also helps prevent residual electrical signals present in the muscle tissue as a result of the pacer stimulation from being interpreted as P-waves or R-waves.

Still referring to FIG. 1, the pacer 10 also includes a memory circuit 40 which is coupled to the control system 26 by a suitable data/address bus 42. This memory circuit 40 allows certain control parameters, used by the control system 26 in controlling the operation of the pacemaker, to be programmably stored and modified, as required, in order to customize the operation of the pacer 10 to suit the needs of a particular patient. Further, data sensed during the operation of the pacer 10 may be stored in the memory 40 for later retrieval and analysis.

A telemetry circuit 44 is further included in the pacer 10. This telemetry circuit 44 is connected to the control system 26 by way of a suitable command/data bus 46. In turn, the telemetry circuit 44, which is included within the implantable pacer 10, may be selectively coupled to an external programming device 48 by means of an appropriate communication link 50, which communication link 50 may be any suitable electromagnetic link, such as an RF (radio frequency) channel.

Advantageously, through the external programmer 48 and the communication link 50, desired commands may be sent to the control system 26. Similarly, through this communication link 50 and the programmer 48, data (either held within the control system 26, as in a data latch, or stored within the memory 40,) may be remotely received from the pacer 10. In this manner, noninvasive communications may be established with the implanted pacer 10 from a remote, non-implanted, location.

The pacer 10 in FIG. 1 is referred to as a dual-chamber pacemaker because it interfaces with both the atria and the ventricles of the heart. Those portions of the pacer 10 which interface with the atria e.g., the lead 14, the atrial sense amplifier 22, the atrial pulse generator 18, and corresponding portions of the control system 26, are commonly referred to as the atrial channel. Similarly, those portions of the pacer 10 which interface with the ventricles, e.g., the lead 16, the ventricular sense amplifier 24, the ventricular pulse generator 20, and corresponding portions of the control system 26, are commonly referred to as the ventricular channel.

In accordance with the present invention, the pacemaker 10 further includes a physiological sensor 52 which is connected to the control system 26 of the pacer over a suitable connection line 54. While this sensor 52 is illustrated in FIG. 1 as being included within the pacer 10, it is to be understood that the sensor 52 may also be external to the pacer 10, yet still be implanted within or carried by the patient.

A common type of sensor 52 is an activity sensor, such as a piezoelectric crystal, which senses physical motion (activity) of the patient. Such sensor is typically mounted to the can or case of the pacemaker. Other types of physiologic sensors are also known, such as sensors which sense the oxygen content of blood, respiration rate, pH of blood, repolarization time of the heart, and the like. The type of sensor used is not critical to the present invention. Any sensor which is capable of sensing some parameter which is relatable to the physiological rate at which the heart should be beating may be used. Physiological sensors of the type described are commonly used with "rate-responsive" pacemakers in order to adjust the rate (escape interval) of the pacer in a manner which tracks the physiological needs of the patient. Thus, stimulation pulses are generated only on demand (in the absence of naturally occurring cardiac activity) at a rate determined by the physiological sensor.

Figure 2:
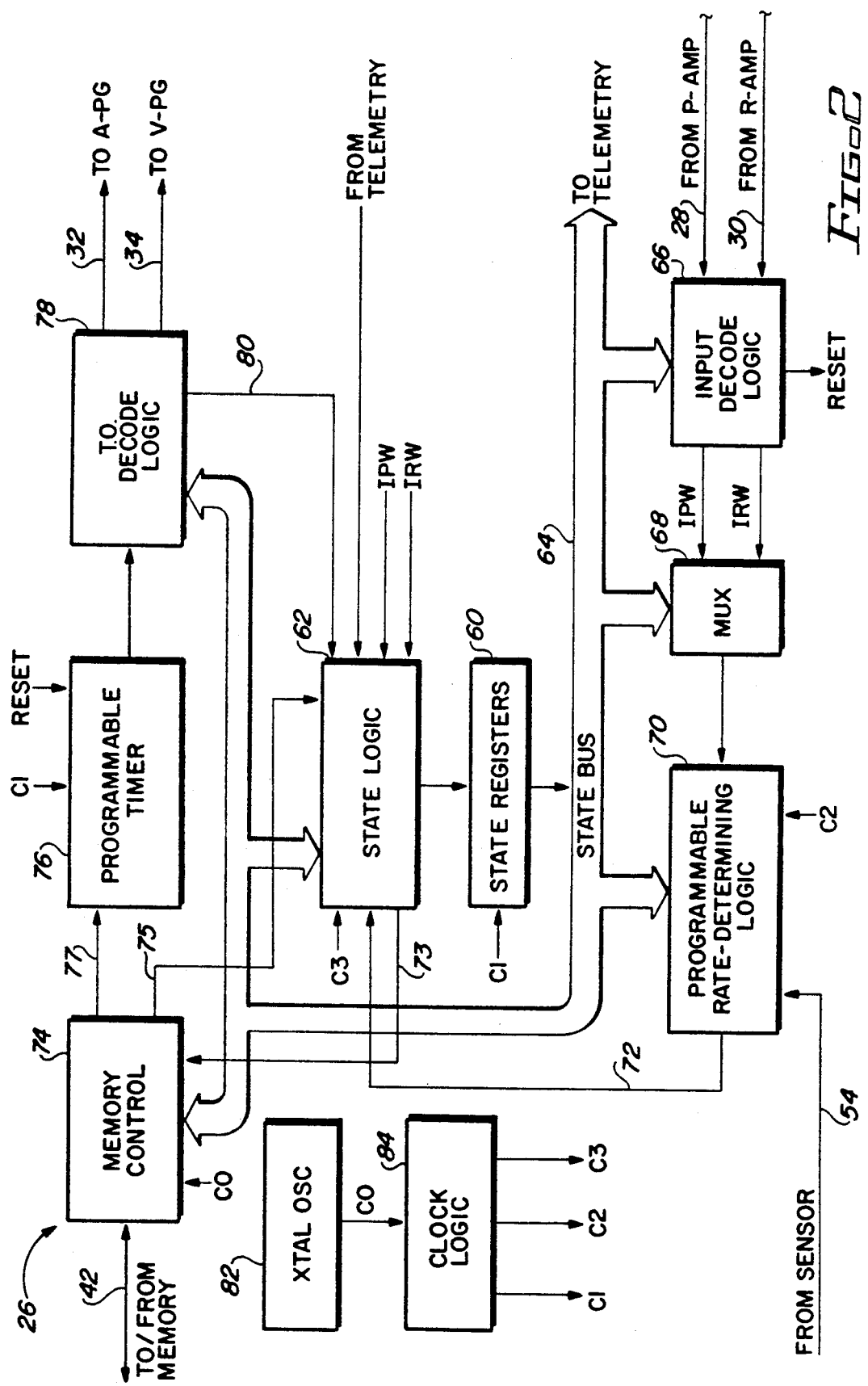
FIG. 2 is a block diagram of one possible embodiment of the control logic of the pacemaker of FIG. 1.

Referring next to FIG. 2, a block diagram of one embodiment of the control system 26 of the pacer 10 is illustrated. It is noted that other embodiments of a control system 26 may also be utilized, such as a microprocessor-based control system. A representative microprocessor-based system is described, for example, in U.S. Pat. No. 4,940,052, entitled "Microprocessor Controlled Rate-Responsive Pacemaker Having Automatic Rate Response Threshold Adjustment," assigned to the same assignee as is the present application. The '052 patent is incorporated herein by reference.

The control system shown in FIG. 2 is based on a state machine wherein a set of state registers 60 define the particular state of the pacer 10 at any instant in time. In general, and as an overview of state machine operation, each state, by design, causes a certain activity or function to be carried out. Several states are executed in a sequence during a given cardiac cycle. The sequence of states which is executed in a particular cardiac cycle is determined by the particular events which occur, such as the sensing of a P-wave or an R-wave, as well as the current state, as certain states can only be entered from certain other states.

Only one state may exist at any instant of time, although several different state machines (or control systems) may operate in parallel to control diverse functions. For example, the telemetry circuit 44 (FIG. 1) preferably utilizes its own state machine, such as is described in the above-cited '052 patent. This telemetry circuit state machine operates essentially independently of the control system state machine shown in FIG. 2.

At the heart of the control system 26 is the state logic 62. It is the state logic which controls the "state" of the state registers 60 and hence the function or operation which will next be carried out by the system. The state logic 62 receives as inputs the current state of the state registers 60, made available over a state bus 64 (which state bus 64 directs the state of the system to several sections of the control system), as well as other signals indicating the current status of the system or events which have occurred.

The output signals from the P-AMP 22 (FIG. 1) and the R-AMP 24 (FIG. are directed to an input decode logic circuit 66. The input decode logic circuit 66 generates appropriate logic signals "IPW" (Inhibiting P-

Wave) and "IRW" (Inhibiting R-Wave) which are selected by a multiplexer 68 and sent to rate-determining logic 70. These signals are also sent to the state logic 62. The function of the rate-determining logic 70 is to determine the rate at which either the IPW or IRW signals are occurring.

A signal representative of this rate is sent, as an output signal from the rate determining logic 70, to the state logic 62 over a signal line 72. The rate-determining logic 70 further receives a sensor rate signal from the sensor 52 (FIG. 1), and (depending upon the particular state of the system, as defined by the state registers 60, and as made available to the rate-determining logic 70 over the state bus 64) sends a rate signal to the state logic 62 over signal line 72 indicative of this sensor rate.

Still referring to FIG. 2, a memory control circuit 74 provides the needed interface between the circuits of the control system 26 and the memory 40 (FIG. 1). This memory control circuit 74 may be any conventional memory access circuit which sends or receives data to or from memory at a specified address. Data retrieved from the memory 40 may be sent to either the state logic 62 over signal line(s) 75 or to a programmable timer 76 over a signal line(s) 77. Data sent to the memory 40 may be either the current state of the system (obtained off of the state bus 64), or other selected signals from the state logic 62 (as made available over signal line(s) 73).

The function of the programmable timer 76 is to define a prescribed time interval, the length of which is set by the signal(s) received from the memory control 74 over the signal line(s) 77, and the starting point of which begins coincident with the start of the current state, as obtained from the state bus 64. The timer 76 further generates a time-out signal when this prescribed time interval has elapsed.

During this prescribed time interval, the timing function may be reset by a reset signal, typically obtained from the input decode logic 66, although some states (as obtained from the state bus 64) may also effectuate an immediate reset of the timer 76. The time-out signal is sent to a time-out decode logic 78. It is the function of the time-out decode logic 78 to generate the appropriate trigger signals which are sent to the A-pulse generator 18 or the V-pulse generator 20 (FIG. 1). Further, an appropriate logic signal(s) is sent to the state logic 62 by the time-out decode logic 78 over the signal line(s) 80 in order to notify the state logic 62 that the respective trigger signals have been generated.

An oscillator 82, preferably a crystal-controlled oscillator, generates a basic clock signal C0 which controls the operation of the system logic. This clock signal C0 is sent to clock logic circuits 84, where other appropriate clock signals, such as clock signals C1, C2 and C3, are generated, all derived from the basic clock signal C0. These clock signals are distributed throughout the control system 26 in order to appropriately synchronize the various events and state changes which occur within the pacemaker.

The rate of the basic clock signal C0 is not critical to the present invention. In general, a rate of 25-40 Khz for the basic clock rate C0 is adequate. This rate provides a basic time increment of 25-40 microseconds each clock cycle, and this is more than enough time to effectively control the pacemaker operation. If desired, a faster basic clock rate may be used, particularly by the memory control 74, to speed up the data transfer between the control system 26 and the memory 40, although for most pacemaker operations, a fast data transfer rate is not essential.

In operation, the control system of FIG. 2 starts at an initial state, wherein the state registers 60 assume a prescribed value which defines the initial state. For example, assuming four flip-flops are used for the state registers 60, an initial state might be "1000" (hexadecimal "8") wherein the first flip-flop assumes a "1" state, and the remaining three flip-flops each assume a "0" state. This state may be defined as a V-A Delay (VAD) state wherein a prescribed VA interval is initiated. This interval may be considered as the "escape interval" mentioned previously.

As soon as the memory control 74 detects that the VAD state has been initiated, as evidenced by the "1000" appearing on the state bus 64, it retrieves from the memory 40 an appropriate data word, previously programmed into the memory 40 from the external programmer 48, which defines the desired length of the V-A delay. This data word is sent to the programmable timer and sets the length of the time period which is to be measured during the VAD state.

The timer 76 is essentially just a counter which counts down (or counts up), using a specified clock signal, to the value specified in the data word. When the counting has been completed, and assuming that the counter has not been reset by the occurrence of a P-wave or an R-wave, the counter or timer 76 is said to have "timed-out," and an appropriate time-out signal is generated which is sent to the time-out decode logic 78.

The decode logic 78, in turn, recognizes that the current state of the system is the VAD state (as determined by monitoring the state bus 64), and therefore that the VA interval (escape interval) has timed out without any cardiac activity having been sensed, generates an A-pulse trigger signal, sent to the A-pulse generator 18, so that the atrium can be stimulated. At the same time, an appropriate logic signal(s) is sent to the state logic 62 over the signal line(s) 80 to alert the state logic to the fact that the timer 76 has timed out.

The state logic 62, in response to receiving the signal(s) from the time-out decode logic 78, and also in response to the current VAD state, triggers the next state of the prescribed sequence. For DDD operation, this state is typically a blanking state, or BLANK state, during which the P and R sense amplifiers, 22 and 24, are disabled. Accordingly, the state logic generates appropriate signal(s) on signal lines 36 and 38 to blank the atrial sense amplifier 22 and the ventricular sense amplifier 24, respectively, and also causes the state registers 60 to change to a BLANK state, which state could be defined, for example, by the flip-flops of the state registers 62 assuming a "0001" (hex "1") condition.

This BLANK state, detected on the state bus 64, causes the memory control circuitry 74 to retrieve an appropriate data word from the memory 40 which defines the length of the blanking interval, which data word is loaded into the programmable timer 76. As soon as the timer 76 times out, indicating that the prescribed blanking interval has elapsed, a time-out signal is generated which is sent to the time-out decode logic 78. Upon receipt of this time-out signal, and in response to the current state being a BLANK state, the time-out decode logic 78 sends an appropriate logic signal to the state logic 62. The state logic 62 responds by steering the state registers 60 to assume the next state in the prescribed sequence, which may be, for example, an A V Delay (AVD) state. At the beginning of the AVD state, another value is loaded into the programmable timer 76 which defines the length of the AV interval. If the timer 76 times out without being reset, indicating that no P-waves or R-waves have been sensed, the decode logic 78 generates a V-pulse trigger signal, and notifies the state logic 62 of this event. The state logic 62, in turn, causes the next appropriate state to be entered, which state may be another blanking state, or BLANK state, similar to the one described above, but having perhaps a different duration. At the conclusion or timing out of this second BLANK state, the next state in the prescribed sequence is initiated, which state may be a refractory (REF) state.

In the manner described above, the control system 26 assumes one state after another, thereby controlling the operation of the pacemaker In general, a state is changed when the timer 76 times out, or when a prescribed event occurs. For example, if during the VAD state an IPW signal is received (indicating that a P-wave has been sensed), the input decode logic 66 generates a reset signal to reset the timer 76, and the state logic 62 responds by immediately (typically within the next few clock cycles) changing the state to the next appropriate state, for example, an AVD state.

Further, if during the AVD state an IRW signal is received (indicating that an R-wave has been sensed), the input decode logic 66 generates another reset signal to reset the timer 76, and the state logic responds by immediately changing the state to the next appropriate state, for example, a refractory (REF) state. It is noted that the state of the control system 26 could also be changed by receipt of an appropriate command from the telemetry system.

The control system 26 of FIG. 2 may be realized using dedicated hardware circuits, or by using a combination of hardware and software (or firmware) circuits. The appropriate sequence of states for a given mode of operation, such as DDD or VVI, for example, may be defined by appropriate control of the memory control 74 and the state logic 62. These circuit elements, in turn, are most easily controlled through an appropriate software or firmware program which is placed or programmed into the pacemaker memory circuits. The manner of accomplishing such programming is well known in the art. A detailed description of the various circuits of the control system 26 of FIG. 2 will not be presented herein because all such circuits may be conventional, or may be patterned after known circuits available in the art. Reference is made, for example, to the above-referenced '555 patent, to Thornander et al., wherein a state-machine type of operation for a pacemaker is described; and to the '980 patent, to Mann et al., wherein the various timing intervals used within the pacemaker and their interrelationship are more thoroughly described.

The operating states of a typical dual-chamber programmable pacemaker may have up to eighteen states associated with its control system. These states are described fully in the above-referenced patents. A summary of these states is presented below in Table 1.

TABLE 1

States of the Pacemaker Control System

| State | Symbol | Description |
| --- | --- | --- |
| 0 | APW | A-Pulse (A-Pulse triggered) |
| 1 | BLANK | V-Sense Input Inhibit (Blank) |
| 2 | AREF | A Refractory |
| 3 | SIPW | Sensed Inhibiting P-wave (P-wave sensed) |
| 4 | AVD | A-V Delay |
| 5 | CROSS | Crosstalk Sense |
| 6 | VPW | V-Pulse (V-Pulse triggered) |
| 7 | SIRW | Sensed Inhibiting R-wave (R-wave sensed) |
| 8 | VAD | V-A Delay |
| 9 | SHORT1 | Shorten A-V Delay a first prescribed amount if IPW during SHORT1 with Physiologic A-V Delay On |
| A | MTR | Max Track Rate |
| B | SHORT2 | Shorten A-V Delay a second prescribed amount if IPW during SHORT2 with Physiologic A-V Delay On |
| C | RRT | Lengthen VA interval if at low battery |
| D | RNOISE | R Noise sensed during VREF or RNOISE |
| E | LIPW | Latched IPW -- P-wave sensed in MTR |
| F | PNOISE | P Noise sensed during AREF or PNOISE |
| (none) | VREF | V Refractory, independent 1-bit state machine synchronized to pulse generator when AREF starts |
| (none) | ABSREF | Absolute Refractory for a prescribed period, starts when AREF starts |

In addition to the states identified above in Table 1, a dual-chamber pacemaker made in accordance with the present invention preferably incorporates at least two additional states: (1) an ACP (Atrial Competition Prevention) state, and an ARV (Atrial Rate Verify) state, as will become evident from the description that follows.

With the foundation of a dual-chamber, rate-responsive, programmable pacemaker now established, the present invention will be more fully described. Broadly speaking, one embodiment of the invention may be characterized as a system for preventing atrial competition in a rate-responsive, dual-chamber pacemaker configured to operate in a DDDR mode of operation. Such system includes: (a) means for defining a physiological pacing rate; (b) control means for generating timing signals indicative of when an atrial and/or ventricular stimulation pulse should be generated by the pacemaker in order to maintain the physiological pacing rate; (c) sensing means coupled to the control means for sensing atrial and ventricular activity, such as P-waves, indicating natural atrial activity, and R-waves, indicating natural ventricular activity, the control means generating the timing signals needed to generate atrial and/or ventricular stimulation pulses on demand as needed in the absence of intrinsic P-waves and/or R-waves; and (d) stimulation pulse generating means coupled to the control means for generating the atrial and/or ventricular stimulation pulses in response to the timing signals. The control means in such embodiment may be characterized as comprising: (i) PVARP generating means for generating a post ventricular atrial refractory period (PVARP) subsequent to the generation of each ventricular stimulation pulse or the sensing of an R-wave, the PVARP defining a time interval during which sensed atrial activity is not considered as a valid P-wave, and (ii) atrial pulse prevention means generates an atrial stimulation pulse from being generated that is in competition with atrial activity sensed during the PVARP. Advantageously, the atrial pulse prevention of such embodiment occurs without changing the timing signals that control when a ventricular stimulation pulse is generated in order to maintain the physiological pacing rate.

In one particular embodiment of this invention, the atrial pulse prevention means generates an atrial competition prevention (ACP) interval in response to atrial activity sensed during the PVARP. Such ACP interval has a prescribed duration. The generation of any atrial stimulation pulses during the ACP interval is inhibited or delayed until the end of the ACP interval. Hence, an atrial pacing pulse is not generated in competition with sensed atrial activity that occurs during the PVARP for at least the duration of the ACP interval.

Figure 3:
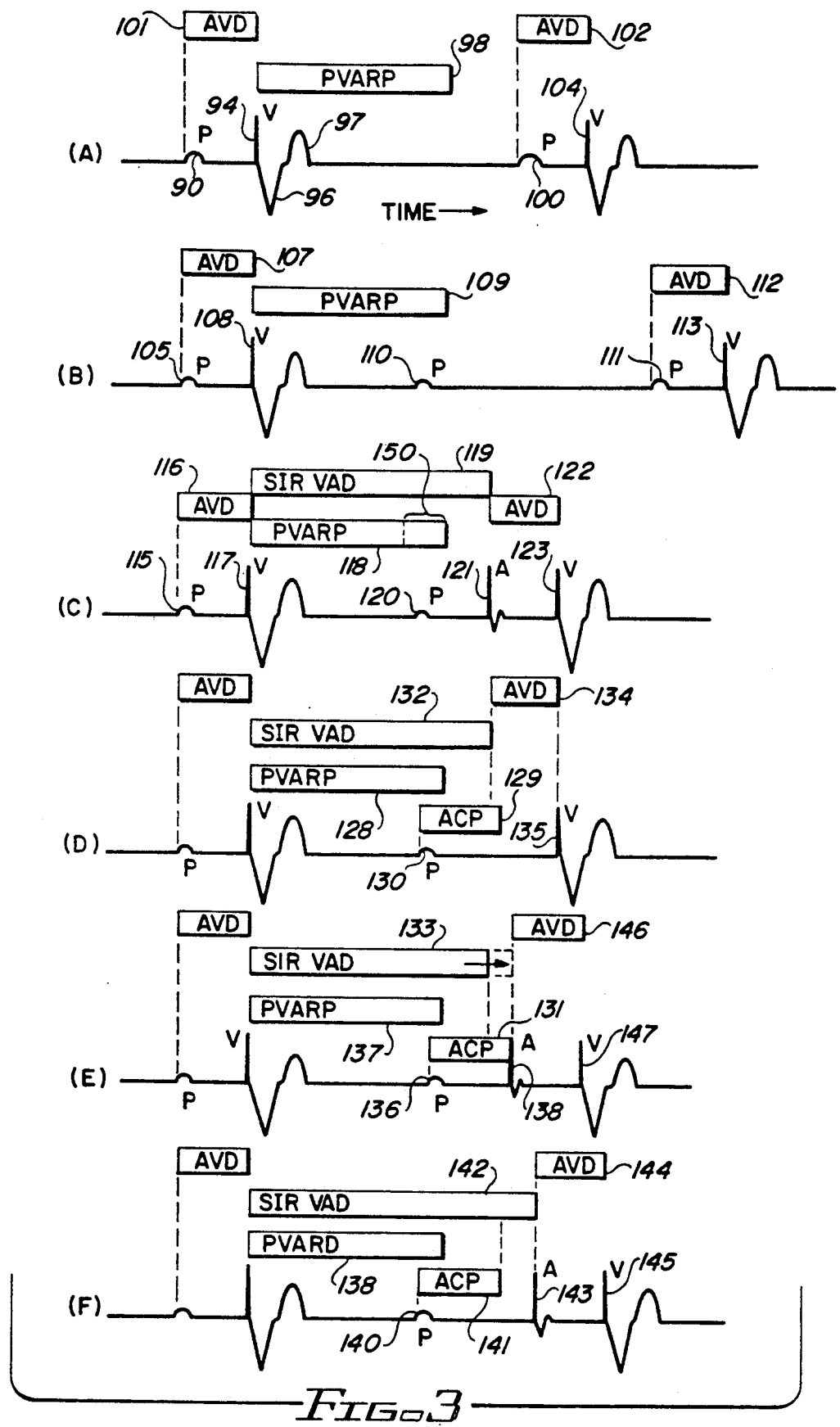
FIG. 3 is a timing diagram illustrating a series of waveforms and pacemaker timing intervals (A)–(F) that depict the problem of atrial competition, and further show how variations of one embodiment of the present invention addresses this problem by generating an atrial competition prevention (ACP) interval.

The operation of such atrial pulse prevention means is best illustrated with reference to FIG. 3. FIG. 3 shows a timing diagram illustrating a series of waveforms and pacemaker timing intervals, labeled (A)–(E). In general, these series of waveforms depict the problem of atrial competition, and further show how the generation of an atrial competition prevention (ACP) interval minimizes such problem.

It is noted that in the timing and waveform diagrams of FIG. 3, several events are shown as a function of time. In each of the five different sequences of events shown in FIG. 3, cardiac events are represented by an electrocardiograph (ECG) schematic that includes P-waves, A-pulses, or V-pulses. The little "bump" by the letter "P" represents a P-wave. The vertical line by the letter "V" represents a V-pulse. The large waveform following a V-pulse represents the QRS-T waves that accompany a stimulated ventricular depolarization. The vertical line by the letter "A" represents an A-pulse. Timing intervals, time periods, or time delays, generated by the pacemaker control system, i.e., the state logic, are represented as boxes or rectangles above the ECG waveform. For simplicity, only time intervals relevant to the present invention are shown. A given timing interval has a relative duration within the cardiac cycle as shown in the figure. That is, a given timing interval begins at that instant of time coincident with its left edge, and terminates at that instant of time coincident with its right edge, with time being the horizontal axis and increasing to the right.

In the upper waveform diagram of FIG. 3, labeled (A), hereafter referred to as FIG. 3(A), conventional atrial rate based pacing (P-wave tracking) is shown. During such pacing, the occurrence of a P-wave 90 causes the A-V delay (AVD) 92 to begin, i.e., causes the AVD state to be entered. At the conclusion of the A-V delay 92, a V-pulse 94 is issued. The generation of the V-pulse 94, in turn, causes the ventricles to contract, represented by the QRS wave 96 and T-wave 97. Also, the generation of the V-pulse causes the post ventricular atrial refractory period (PVARP) 98 to be generated. During the PVARP 98, no atrial activity can be sensed; or, if it is sensed, it is not treated as a P-wave. For the situation shown in FIG. 3(A), no P-waves occur during the PVARP 98. However, after PVARP has terminated, a P-wave 100 occurs. This P-wave 100 is sensed by the pacemaker circuits as a P-wave, and causes another A-V delay 102 to be initiated. At the conclusion of the A-V delay, a V-pulse 104 is issued, causing the ventricles to again depolarize. This process continues, with each V-pulse being issued one A-V delay after the sensing of a P-wave. Thus, the ventricle is paced at a rate that tracks the sensed P-waves.

In FIG. 3(B), a condition is shown where it is assumed that intrinsic P-waves occur at a relatively rapid rate, e.g., as might occur during physical exercise. A first P-wave 105 is sensed and triggers the A-V delay 107, after which a V-pulse 108 is issued. The V-pulse 108 causes the ventricles to contract, and also initiates the PVARP 109. A second P-wave 110 occurs during the PVARP 109. Thus, in a conventional DDD pacemaker, the P-wave 110 is not recognized by the pacemaker logic circuits as a P-wave, but is rather considered as noise. Hence, the pacemaker logic circuits are not aware that P-wave 110 has occurred, and they remain armed in an appropriate waiting state, waiting for the next P-wave to occur, or for the applicable escape interval to time out, whichever occurs first. Because, the intrinsic P-wave rate is relatively fast, a third P-wave 111 occurs after the expiration of the PVARP 109, and before the appropriate escape interval times out. Hence, the P-wave 111 is sensed, causing the A-V delay 112 to be initiated. After the A-V delay 112 times out, a V-pulse 113 is generated, causing the desired ventricular contraction. This process continues with every other P-wave being sensed, and tracked. This condition (of sensing every other P-wave) is referred to as 2:1 block. It is not desirable to remain in a 2:1 block condition for any sustained period of time because the heart is only being paced at a rate that is one half as fast as it should be in order to pump the needed blood supply through the body to meet the physiological demands manifest by the rapid intrinsic P-wave rate.

In order to alleviate the problem of 2:1 block, as well as other problems, the DDDR pacing mode may be used. Operation in a DDDR pacing mode is depicted in FIG. 3(C). In such a pacing mode, it is again assumed that there is a relatively fast intrinsic P-wave rate. A first P-wave 115 is sensed, causing the A-V delay 116 to be generated. At the conclusion of the A-V delay 116, a V-pulse 117 is issued, and a PVARP 118 is initiated, as described previously. However, because a DDDR pacing mode is being used, the V-pulse 117 also causes a sensor-indicated rate (SIR) V-A delay (VAD) 119 to be operative. This SIR VAD 119 essentially represents the escape interval of the pacemaker as determined from the physiologic sensor. Because there is a relatively fast intrinsic P-wave rate, which fast P-wave rate evidences a high physiologic demand, the SIR VAD 119 will also represent a high physiologic demand, assuming the physiologic sensor is functioning properly. That is, the SIR VAD will not be very long. Thus, as shown in FIG. 3(C), even though the next P-wave 120 occurs during PVARP 118, and is thus not sensed (as was the case in FIG. 3(B) above), the SIR VAD 119 terminates soon after the termination of PVARP, causing an A-pulse 121 to be generated. The generation of the A-pulse 121 triggers an A-V delay 122, after which a V-pulse 123 is generated, thereby allowing the heart to be paced at a relatively rapid rate commensurate with the sensed physiological need for a rapid heart rhythm.

Unfortunately, the condition shown in FIG. 3(C) creates atrial competition between the P-wave 120 and the A-pulse 121. Atrial competition is not desirable for the reasons previously explained. Advantageously, the present invention prevents such atrial competition using the techniques and/or methods described below.

In accordance with an atrial competition prevention (ACP) embodiment of the invention, atrial activity is sensed during the PVARP (at least during the relative refractory portion of the PVARP). The sensing of atrial activity during PVARP causes an atrial competition prevention (ACP) time interval to be generated, i.e., causes an atrial competition prevention state to be entered by the state logic that lasts for a prescribed period of time. The prescribed duration of the ACP interval, or state, is fixed, e.g., on the order of 250-350 milliseconds, as selected by a physician at the time of programming the pacemaker. The pacemaker logic is configured so that during the ACP interval, no atrial stimulation pulse, A-pulse, can be generated, even if one is called for by the SIR VAD (sensor-driven escape interval). If the SIR VAD times out during the ACP interval, the A-pulse is inhibited, but the A-V delay is initiated as though an A-pulse had been issued. Or, alternatively, the SIR VAD is simply extended until the end of the ACP window. If the SIR VAD times out after the expiration of the ACP interval, an A-pulse is issued in normal fashion. This assures that there will always be a time interval equal to at least the duration of the ACP interval between any atrial activity sensed during the PVARP and an A-pulse, thereby minimizing the likelihood of atrial arrhythmia induction due to competition.

Operation of the ACP embodiment of the invention is shown in FIGS. 3(D), 3(E), and 3(F). In FIG. 3(D), a P-wave 130 occurs during the PVARP 128. Thus, an ACP interval 129 is initiated. Before the timing out of this ACP interval 129, the SIR VAD times out. Hence, no A-pulse is generated. However, an A-V delay 134 is initiated at the conclusion of the SIR VAD. When the A-V delay 134 times out, a V-pulse 135 is generated, thereby continuing to pace the heart at the sensor-driven rate, despite the fact that no A-pulse was generated.

In FIG. 3(E), a P-wave 136 likewise occurs during the PVARP 137. Hence, an ACP interval 131 is initiated. In accordance with the variation of the invention illustrated in FIG. 3(E), the associated SIR VAD 133 is extended to the end of the ACP interval 131. An A-pulse 139 is generated at the end of the SIR VAD 133, i.e., at the end of the ACP interval 131. As is normal, an A-V delay 143 is generated when the extended SIR VAD 133 times out. When the A-V delay 146 times out, a V-pulse 147 is generated, thereby pacing the heart at a rate that is slightly modified from the sensor-driven rate.

In FIG. 3(E), a p-Wave 140 likewise occurs during a PVARP 138, thereby initiating an ACP interval 141. When the ACP interval 141 times out, the SIR VAD 142 has not timed out. Hence, at the timing out of the SIR VAD 142, an A-pulse 143 is generated, causing the A-V delay 144 to start. At the conclusion of the A-V delay 144, a V-pulse 145 is generated. Thus, the heart is paced at the sensor-driven rate.

It is noted that in all of the sequences shown in FIG. 3, it is assumed that there is no natural ventricular activity. However, it is to be understood that should an R-wave be sensed during the A-V delay, no V-pulse will be generated. That is, the pacemaker delivers stimulation pulses to the heart, whether A-pulses or V-pulses, only on demand as indicated by the SIR VAD or AVD. However, even when an A-pulse is demanded at the conclusion of the SIR VAD, such will not be provided unless the ACP interval has also timed out.

In another particular embodiment of the invention, referred to as an atrial rate verify (ARV) embodiment, two additional variations of the invention are provided.

In a first ARV variation, the atrial pulse prevention means includes: (a) rate determining means for determining an intrinsic atrial rate; (b) first comparison means for determining if the sensed intrinsic atrial rate is approaching a reference rate; and (c) means responsive to the first comparison means for shortening the duration of the PVARP. Shortening PVARP in this manner allows atrial activity to be sensed and recognized by the pacemaker logic circuitry as a valid P-wave, thereby inhibiting the generation of any atrial stimulation pulse in accordance with conventional demand pacemaker operation. For example, with reference to FIG. 3(C), if the PVARP 118 is shortened by an amount represented by the portion 150, then P-Wave 120 is sensed, and the A-pulse 121 would be inhibited in conventional demand pacemaker operation.

In a second ARV variation, the atrial pulse prevention means includes: (a) rate determining means for determining an intrinsic atrial rate; (b) first comparison means for determining if the sensed intrinsic atrial rate is equal to or greater than a reference rate; and (c) means responsive to the first comparison means for changing the duration of the PVARP as an inverse function of the sensor-indicated rate, or SIR. That is, the duration of the PVARP is inversely tied to the SIR. Thus, if the SIR increases, the PVARP is shortened, and the benefits of a shortened PVARP are obtained as in the first ARV variation described above. However, as the SIR decreases, returning to its initial value, the PVARP lengthens, also returning back to its initial value. The manner in which the PVARP is controlled by the SIR is controlled by an appropriate algorithm, which algorithm could, of course, be programmed on or off. When on, there is a prescribed relationship between the SIR and PVARP. For example, the algorithm may be such that for every 10 ppm (pulses per minute) increase in the SIR, the PVARP is reduced by 10-20 milliseconds. Of course, these values are only exemplary, and any suitable inverse relationship could be set between the SIR and the PVARP.

Thus, in operation, the ARV embodiments of the invention monitor the rate of the intrinsic P-waves. If such rate is increasing sufficiently to likely place a P-wave within the normal PVARP, then an ARV state is entered by the state logic that either causes the PVARP to be shortened by a prescribed amount, such as 50 to 100 milliseconds, or that shortens the PVARP by an amount dictated by the increase in the SIR. By preventing the intrinsic P-wave from falling within the PVARP (by shortening the normal PVARP), the intrinsic P-wave is sensed as a P-wave, and such sensing inhibits any A-pulse generation in conventional demand pacemaker operation. If the monitored intrinsic P-wave rate subsequently slows down so that there is no danger of the P-waves falling within the normal PVARP, then the shortened PVARP is extended back to the normal PVARP, either in a single step or gradually as the SIR rate returns to normal. That is, as the P-wave rate subsequently slows down, the ARV state is ended, and the pacemaker returns to its normal DDDR operation.

Figure 4:
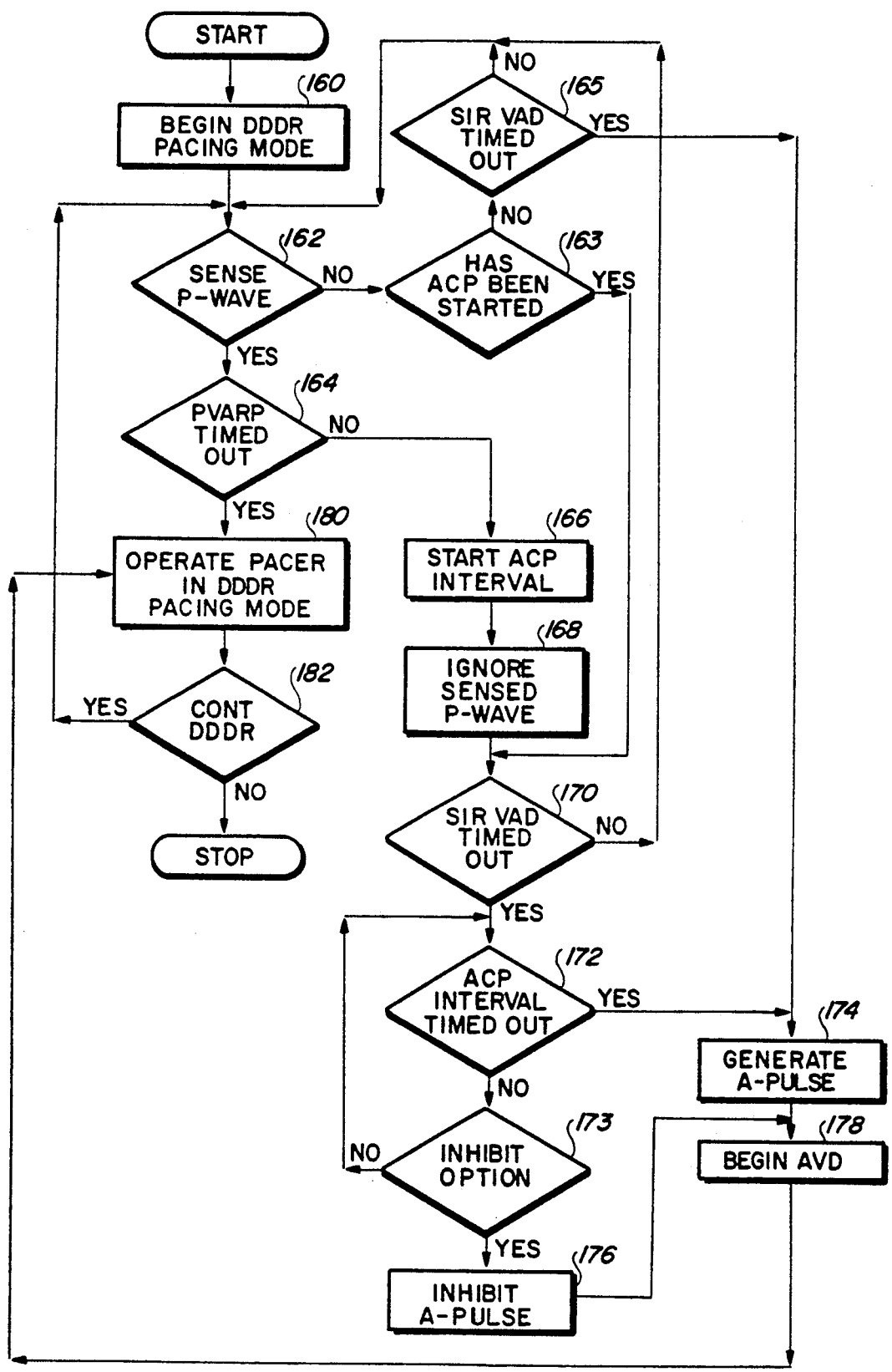
Figure 5:
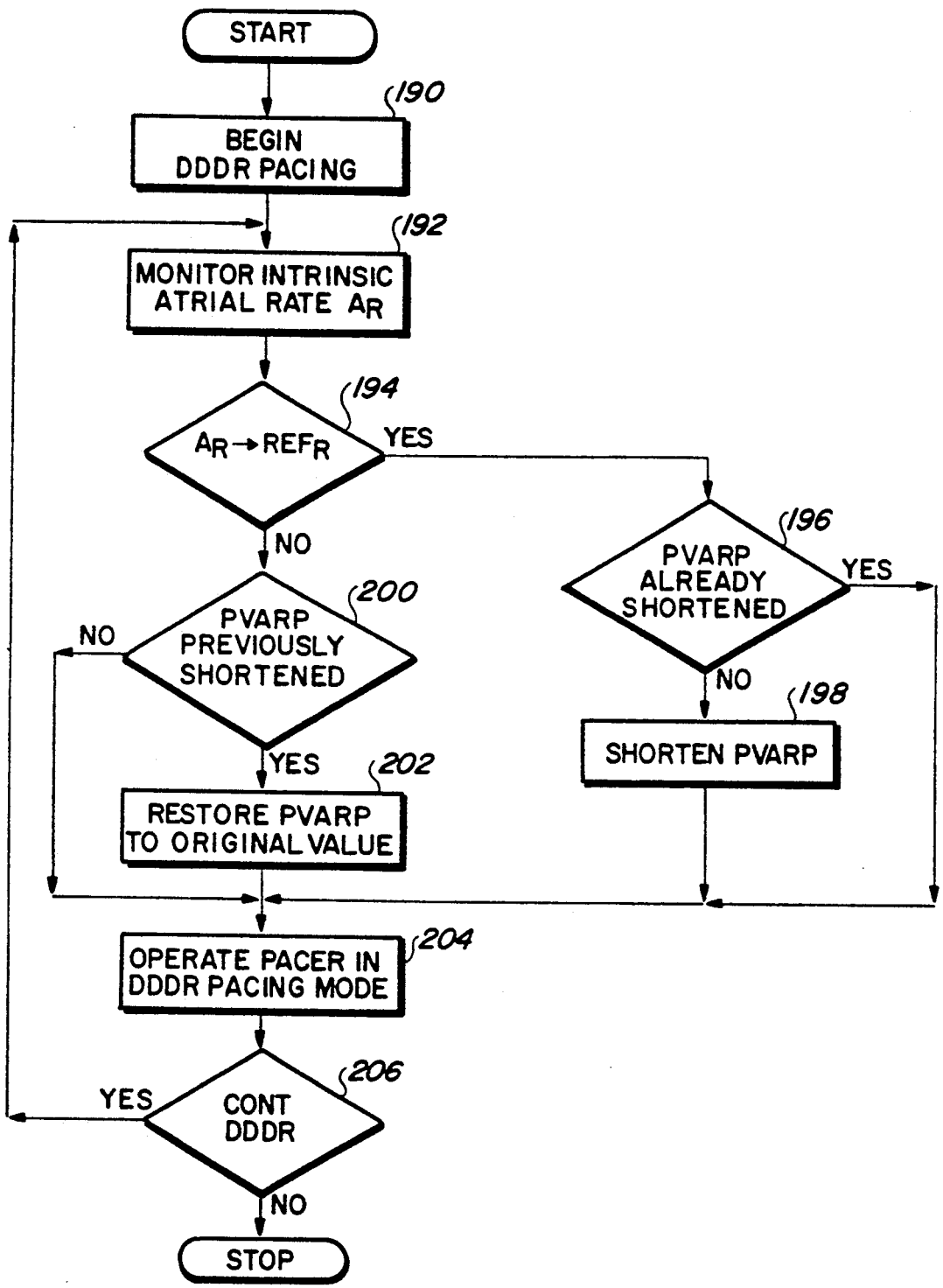
Figure 6:
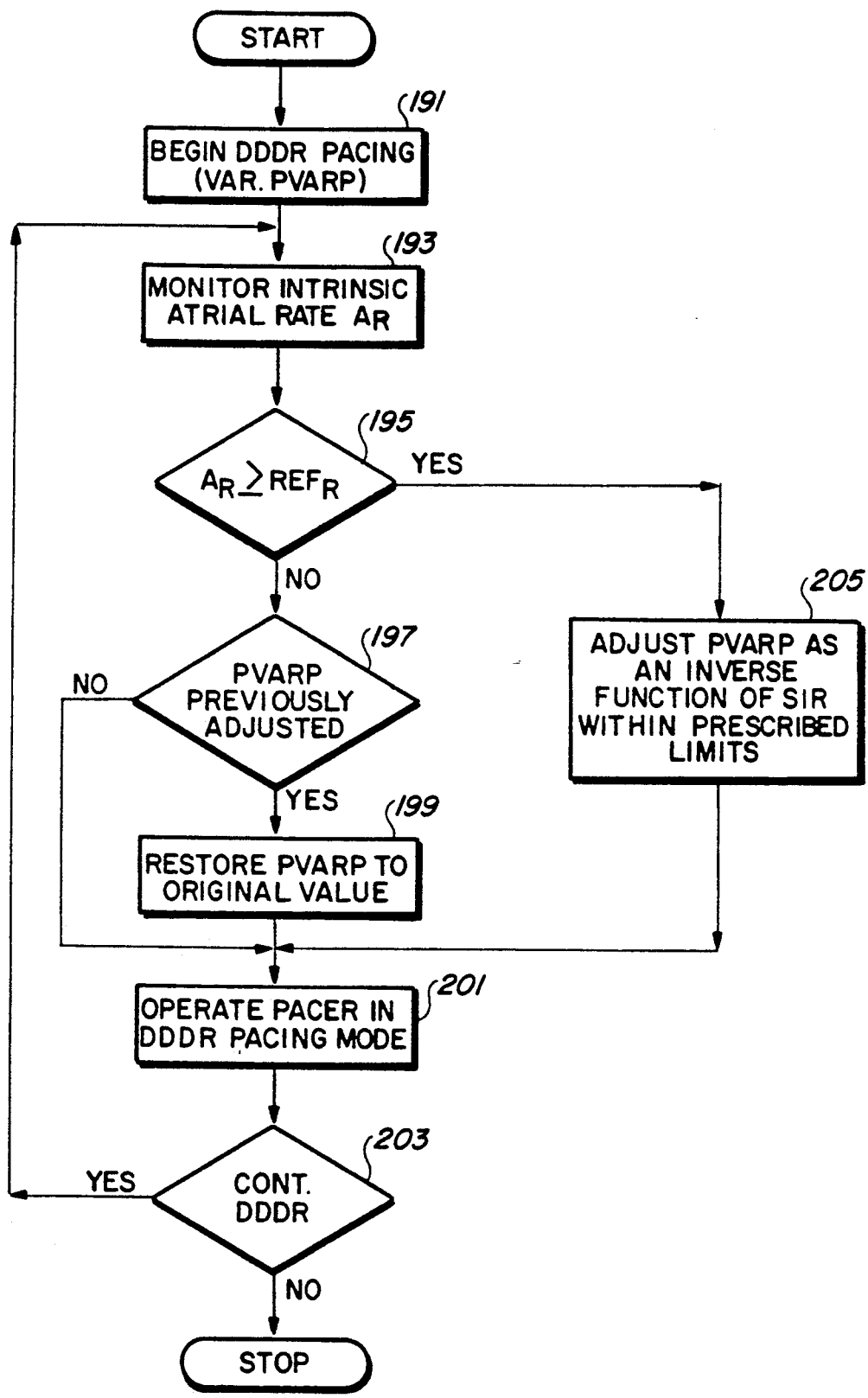

Referring next to FIGS. 4, 5 and 6, flowchart diagrams illustrating a method of operating the pacemaker of FIG. 1 in accordance with the ACP, ARV, and other embodiments of the invention, is shown. The method shown in FIG. 4 shows the ACP embodiment described above. The method shown in FIG. 5 is the first version of the ARV embodiment described above. The method shown in FIG. 6 is the second version of the ARV embodiment described above. These embodiments are aimed at alternative methods of preventing atrial competition, which atrial competition may cause atrial arrhythmias. In contrast, the method shown in FIG. 7 is aimed at accurately detecting an atrial arrhythmia, and responding to such arrhythmia, once detected. It is noted that the method shown in FIG. 7 may be practiced alone or in combination with the methods shown in FIGS. 4, 5 or 6.

In each flowchart, it is noted that the various steps of the particular method being depicted are shown in abbreviated form in "blocks" or "boxes," each of which has a reference numeral associated therewith.

Referring to the flowchart shown in FIG. 4, for example, a method of operating a rate-responsive, dual-chamber pacemaker is shown that avoids generating atrial stimulation pulses that might compete with natural atrial activity. It is understood that the pacemaker is programmed to operate in a DDDR mode of operation, and in fact such is shown as a first step (block 160) in FIG. 4. Basically, the method includes the steps of: (a) sensing intrinsic P-waves; (b) determining if a given sensed intrinsic P-wave occurred during a post ventricular atrial refractory period (PVARP) associated with the programmed DDDR mode of operation of the pacemaker, such PVARP being generated by the pacemaker subsequent to any sensed or paced ventricular activity; (c) in the event that a sensed intrinsic P-wave does occur during PVARP, as determined in step (b), starting an atrial competition prevention (ACP) period; and (d) inhibiting any atrial stimulation pulse in the event the ACP period, if any, has not timed out by the time the atrial stimulation pulse would otherwise be generated by the programmed DDDR mode of operation, or alternatively, delaying the generation of the atrial stimulation pulse until the ACP period has timed out.

More particularly, and as shown in FIG. 4, assuming that the DDDR pacing mode has been initiated (block 160), the method includes as a next step sensing any P-waves (block 162). The term "P-wave" as used in FIG. 4 (and the other flowcharts) is intended to mean "atrial activity". If a P-wave is sensed, then a determination is made as to whether the PVARP has timed out (block 164). If so, then the pacemaker operates in accordance with the conventional DDDR pacing mode (block 180), i.e., an A-pulse is generated at the conclusion of the SIR VAD only if another P-wave is not sensed before the timing out of the SIR VAD, with a V-A delay being initiated by any atrial activity, either the sensing of a P-wave, or the generation of an A-pulse; and with a V-pulse being generated at the conclusion of the A-V delay only if an R-wave is not sensed before the timing out of the A-V delay.

If the PVARP has not timed out (block 164) upon the sensing of a P-wave (block 162), then an ACP interval is initiated. As indicated above, the ACP interval is a fixed interval having a preferred duration of around 300 milliseconds, although for some patients it may be appropriate to have a duration of between 250 and 350 milliseconds, or other values. The duration of the ACP interval may be fixed by the manufacturer of the pacemaker, or programmably set by the physician at implant (and adjusted by the physician, as necessary, thereafter). Once the ACP interval is started, the sensed P-wave (sensed at block 162) is ignored (block 168), i.e., its occurrence has no further effect, and a determination is made as to whether the SIR VAD has timed out (block 170). If not, then the sensing circuits remain active to sense if a P-wave does occur (block 162).

If a P-wave is not sensed (block 162), a determination is made as to whether the ACP interval has been started (block 163). Such determination only has applicability to a "second pass" through the P-wave sensing determination block (block 162). A "second pass" occurs when a P-wave was sensed (block 162) during a "first pass," the PVARP had not timed out (block 164), the ACP interval was started (block 166), and the SIR VAD had not timed out (block 170), thereby returning control for the "second pass" through the P-wave sensing determination block (block 162). If, after such second pass, the ACP has been started (block 163), then a determination is made as to whether the SIR VAD has timed out (block 170).

Once the SIR VAD times out, another determination is made as to whether the ACP interval, if any, has timed out (block 172). If not, a determination is made as to whether the inhibit option has been selected (block 173). The inhibit option is the option described above in connection with FIG. 3(D) where the A-pulse is inhibited. If the inhibit option is selected, then the A-pulse is inhibited (block 176). If the inhibit option has not been selected (block 173), then the delay option, described above in connection with FIG. 3(E), is presumed to be selected. As such, nothing happens until the ACP interval times out, as determined at block 172.

Upon the timing out of the ACP interval (block 172), an A-pulse is generated (block 174). In either event, i.e., after the generation of an A-pulse (block 174) or the inhibiting of an A-pulse (block 176), the A-V delay is begun thereafter (block 178), and the pacer continues to operate in the normal DDDR mode (block 180). If DDDR pacing is to continue (block 182), which is a programmable selection, then the process repeats, with the sensing circuits eventually being placed in a state that allows them to sense a P-wave (block 162) at the appropriate time during the DDDR pacing cycle.

Note from FIG. 4, that so long as a P-wave is sensed, and the PVARP has not timed out, the ACP interval will be started. If an ACP interval has previously been started, then the ACP interval is restarted. In this manner, the latest atrial activity sensed during the PVARP triggers (restarts) the ACP interval. Hence, no A-pulse can be generated until at least the timing out of the ACP interval after the latest atrial activity that occurs during the PVARP.

Note also from FIG. 4 that if a P-wave is not sensed (block 162), and the ACP has not been started (block 163), then a determination is made as to whether the SIR VAD has timed out (block 165). If it has not timed out, then the system continues to look for the occurrence of a P-wave (block 162). If it has timed out, then an A-pulse is generated (block 174), in conventional demand pacer operation.

Referring next to FIG. 5, an alternative method is illustrated aimed at reducing the likelihood of atrial competition in a rate-responsive, dual-chamber pacemaker programmed to operate in a DDDR mode of operation. Essentially, this method includes the steps of: (a) sensing intrinsic P-waves; (b) determining if the sensed intrinsic P-waves are occurring at an intrinsic atrial rate that is increasing and is at least as rapid as a reference rate; (c) in the event that a sensed intrinsic atrial rate is increasing and is at least as rapid as the reference rate, as determined in step (b), shortening a post ventricular atrial refractory period (PVARP) associated with the DDDR mode of operation; and (d) operating the pacemaker in the DDDR mode of operation with the shortened PVARP for so long as the sensed intrinsic atrial rate is equal to or greater than the reference rate.

More particularly, as seen in FIG. 5, after beginning the DDDR pacing mode (block 190), the intrinsic atrial rate, $A_R$, is monitored (block 192). Any conventional means may be used to determine $A_R$. For example, the P-P interval may be measured and averaged over the previous n cardiac cycles, where n is an integer, such as 5. Once $A_R$ has been determined, a determination is made whether $A_R$ is approaching a reference rate, $REF_R$ (block 194). (It is to be understood that although FIG. 5 speaks in terms of monitoring and measuring "rates," the same result is obtained by monitoring and measuring "periods," as one is the simply the reciprocal of the other.) Next, a determination is made as to whether $A_R$ is approaching $REF_R$ (block 194). That is, a determination is made as to whether the rate of the intrinsic P-waves is increasing sufficiently fast so that a given P-wave might fall within the PVARP.

The determination as to whether a given P-wave might fall within the PVARP involves making an estimate based on the trend that has been observed in the increasing intrinsic P-wave rate. This estimate is made using any suitable determining technique. For example, the value of the most recent P-P interval (or the most recent P-P interval average), $PP_i$ is compared with a second most recent P-P interval (or the second most recent P-P interval average), $PP_{i-1}$, in order to determine how much the P-P interval has changed, $\Delta P\text{-}P$. This $\Delta P\text{-}P$ value is then subtracted from $PP_i$ in order to get an estimate of what the next P-P interval, $PP_{i+1}$, is likely to be if this same trend continues. (Note that for an increasing intrinsic P-wave rate, the P-P interval decreases.) This estimate of $PP_{i+1}$ is compared with a corresponding interval, $PP_R$, associated with the $REF_R$. The value of $PP_R$ is selected to be just slightly longer than the ARP. Hence, if $PP_{i+1}$ is less than $PP_R$, it means that the next P-wave will likely fall within PVARP.

Once the determination has been made (at block 194) that $A_R$ is approaching $REF_R$, and hence that a P-wave may soon fall in the PVARP, is automatically shortened (block 198), providing that PVARP has not previously been shortened (block 196). The amount by which PVARP is shortened is programmably selected by the physician, and will typically be 50 to 200 milliseconds. Once PVARP is shortened, the pacer operates in the DDDR pacing mode using the shortened PVARP.

Whether operating the pacer using the shortened PVARP, or using the normal PVARP, the determination (made at block 194) as to whether $A_R$ is approaching $REF_R$ can also be used as an indication as to whether $A_R$ is not approaching $REF_R$, i.e., whether $A_R$ is sufficiently removed from $REF_R$ to assure that the P-waves will not fall within the PVARP. If the P-waves are not likely to fall within the original PVARP, and assuming that PVARP has been previously shortened (block 200), then the value of PVARP is returned to its original value (block 202). Thereafter, the pacer operates in its DDDR mode (block 204), using the normal PVARP or the shortened PVARP, depending on whether the intrinsic P-waves are likely to fall within the normal PVARP or not, until programmed otherwise (block 206).

Referring next to FIG. 6, a variation of the method shown in FIG. 5 is illustrated. The method illustrated in FIG. 6 is essentially the same as method shown in FIG. 5 except that rather than shortening PVARP a prescribed amount upon making a determination that $A_R$ is approaching the reference value $REF_R$, PVARP is adjusted as an inverse function of the sensor-indicated rate, SIR. Thus, upon initiating DDDR pacing using this variable PVARP approach (block 191), the intrinsic atrial rate $A_R$ is monitored (block 193). If a determination is made that $A_R$ is greater than or equal to a reference rate, $REF_R$ (block 195), which reference rate may be quite low, e.g., as low as the at rest rate of the pacemaker, the PVARP is adjusted as a function of the SIR (block 205), and the pacer continues to operate in the DDDR pacing mode (block 201). The relationship between PVARP and the SIR is preferably programmable, and causes the PVARP to shorten a first prescribe amount for each measured increment in the SIR. Thus, for example, an increase in the SIR of 10 ppm causes the PVARP to shorten 10 or 20 milliseconds. Similarly, a decrease in the SIR of 10 ppm causes the PVARP to lengthen 10 or 20 milliseconds.

Should $A_R$ fall below the reference rate $REF_R$ (block 195), then PVARP is restored to its original value (block 199) providing PVARP has not been previously adjusted (block 197). Thus, by selecting $REF_R$ to be an appropriate value, any increase of $A_R$ above $REF_R$ causes PVARP to gradually shorten and then gradually lengthen until $A_R$ is back below $REF_R$, at which time PVARP remains at its original value. However, any initial decreases of $A_R$ below $REF_R$ do not cause the value of PVARP to be change. Thus, PVARP changes as controlled by the SIR only when $A_R$ initially increases, not when it initially decreases.

Referring next to FIG. 7, a still further embodiment of the invention is shown in flowchart form. This embodiment of the invention, like the embodiments described above, provides a method of operating a rate-responsive, dual-chamber pacemaker programmed to operate in a DDDR mode of operation (block 210). In contrast to the methods described above in connection with FIGS. 4, 5 and 6 (which are aimed at preventing atrial competition), the method shown in FIG. 7 is aimed at detecting an atrial arrhythmia and dissociating the ventricular paced rate from it once detected. As previously indicated, such method may be practiced alone or in combination with the methods of FIGS. 4, 5 or 6.

It is understood that the pacemaker with which the method of FIG. 7 is used includes physiological sensor means for defining a sensor-indicated rate (SIR) indicative of a preferred rate at which the pacemaker should pace a patient's heart on demand based on a sensed physiological parameter. Broadly stated, the method comprises the steps of: (a) sensing intrinsic P-waves; (b) determining if the sensed intrinsic P-waves are occurring at a rate that is much greater than the SIR; (c) in the event that a sensed intrinsic atrial rate is greater than the SIR, as determined in step (b), lengthening a maximum tracking interval (MTI) associated with the DDDR mode of operation of the pacemaker, thereby reducing a maximum tracking rate associated with the DDDR mode of operation; and (d) operating the pacemaker in the DDDR mode of operation with the lengthened MTI for so long as the sensed intrinsic atrial rate is equal to or greater than the SIR.

More particularly, and with reference to FIG. 7, it is seen that the method begins with a first step of pacing in a DDDR mode (block 210). Thereafter, the intrinsic atrial rate $A_R$ is monitored (block 212). Even when P-waves occur during PAARP, such P-waves are still monitored so that $A_R$ can be determined. The value of the intrinsic atrial rate, $A_R$, is compared to the sensor-indicated rate, SIR. If $A_R$ is significantly greater than SIR (block 214), the maximum tracking rate (MTR) of the pacemaker is reduced (block 218) providing it has not previously been reduced (block 216). If $A_R$ is not significantly greater than the SIR (block 214), and if the MTR has not been previously reduced (block 222), the pacemaker continues to operate in its DDDR mode (block 220). If the MTR has been previously reduced, but a determination is made (at block 214) that $A_R$ is not significantly greater than the SIR, then the MTR is restored to its original value (block 224), and the pacer thereafter operates in accordance with its DDDR mode (block 220) for so long as the DDDR mode remains as the programmed mode (block 226).

Note, that the maximum tracking rate, or MTR, of a pacemaker is determined by a programmably set maximum tracking interval (MTI), and defines the highest rate at which the pacemaker can track intrinsic cardiac activity in order to provide stimulation pulses on demand. (A more complete description of the MTR, and associated MTI, may be found in the Mann et al. '980 patent, and/or the Thornander et al. '555 patent, previously referenced.)

It is noted that a determination that $A_R$ is significantly greater than the SIR (block 214) provides a reliable indication (assuming that the physiological sensor used with the pacemaker is functioning) that an atrial arrhythmia condition is present. That is, if the fast atrial rate were due to increased physiological demand, then the SIR would increase commensurate with the atrial rate. However, when there is a large disparity between $A_R$ and the SIR, then that is an indication that something is wrong. Advantageously, reducing the maximum tracking rate of the pacer will minimize patient symptoms related to the fast atrial rate. Additionally, should the fast detected atrial rate be related to 1:1 retrograde VA conduction, the reduction in the paced ventricular rate will be beneficial. If the arryhmia stops, then $A_R$ should return to a rate that is close to the SIR, and the MTR can be returned to its original value (block 224). (Note that reducing the MTR is typically realized by increasing the duration of length of the MTI.) The value of $A_R$ required to be above the SIR to produce this response (as determined at block 214) may be preset by the manufacturer or a value programmable by the physician.

Still referring to FIG. 7, if $A_R$ is significantly greater than the SIR (block 214), and if the MTR has already been reduced (block 216), then a further determination is made as to whether $A_R$ has been significantly greater than SIR for a sustained period of time (block 228). A sustained period of time is defined as either a fixed period of time, such as 60 seconds, or a prescribed number of cardiac cycles, m, where m is an integer, such as 150. If a sustained period of time has not elapsed since the MTR was first reduced (as determined at block 228), then the pacer continues to operate in its programmed DDDR mode (block 220). If, however, a sustained period of time has elapsed since the MTR was first reduced, i.e., if the atrial arrhythmia has persisted for the defined sustained time period, then the pacing mode is automatically switched to a single-chamber pacing mode (block 230), such as the VVIR mode. Operation begins in the new mode (block 232) until a reprogramming change is made (block 234), or until the detected atrial rate $A_R$ reduces to an acceptable level (blocks 236–242).

It is noted that if the arrhythmia continues for a sustained period of time (block 228), that is an indication that something is wrong, and switching to an alternate mode (block 230), such as the VVIR mode, advantageously provides the safest and most effective way of dealing with the problem until such time as a physician can thoroughly evaluate exactly what the problem is and what can be done to correct it.

In conclusion, and as described above, it is seen that the present invention provides a dual-chamber pacemaker operating in a sensor-driven mode, and a method of operating such a pacemaker, that prevents atrial arrhythmias. This it does by minimizing the likelihood of atrial competition between naturally occurring P-waves and atrial stimulation pulses. In one embodiment, termed the "ACP" embodiment, the pacemaker senses atrial activity during the pacemaker's post ventricular atrial refractory period (PVARP) and prevents any atrial stimulation pulses from being generated within a prescribed time interval thereafter, thereby minimizing atrial competition by assuring that there is always at least the prescribed time interval between sensed atrial activity and an atrial stimulation pulse. In another embodiment, termed the ARV embodiment, the pacemaker automatically shortens PVARP whenever the sensor-driven rate approaches a rate that might place atrial stimulation pulses near the end of the time in the cardiac cycle when the original (unshortened) PVARP terminates, thereby minimizing atrial competition by increasing the time period (after PVARP) during which atrial activity can be sensed, which atrial activity (if sensed after PVARP) inhibits the generation of an atrial stimulation pulse.

As further seen from the preceding description, the present invention provides a dual-chamber, sensor-driven pacemaker and method of operation that ensures that when an atrial stimulation pulse is provided, it captures the heart. This it does by ensuring that the atrial stimulation pulse is not provided at a time that would compete with a naturally occurring P-wave, during which time the cardiac tissue is refractory and unable to respond properly to the stimulation pulse.

As also seen from the above description, the present invention provides a dual-chamber, programmable, rate-responsive pacemaker that includes selectable means for detecting and responding to an atrial arrhythmia. This is accomplished by programming the pacemaker to detect an atrial arrhythmia whenever there is a large disparity between a sensed atrial rate and a sensor-driven rate. Once such atrial arrhythmia is detected, the pacemaker includes means for automatically reducing the maximum tracking rate of the pacemaker, and-/or switching the pacemaker operating mode from a dual-chamber rate-responsive mode, such as DDDR, to a single-chamber ventricular rate-responsive mode, such as VVIR.

While the invention herein disclosed has been described by means of specific embodiments and applications thereof, numerous modifications and variations could be made thereto by those skilled in the art without departing from the scope of the invention set forth in the claims.

What is claimed is:

1. In a rate-responsive, dual-chamber pacemaker configured to operate in a DDDR mode of operation, a system for preventing atrial competition comprising:
   means for defining a physiological pacing rate;
   control means for generating timing signals indicative of when an atrial and/or ventricular stimulation pulse should be generated by said pacemaker in order to maintain said physiological pacing rate;
   sensing means coupled to said control means for sensing atrial and ventricular activity, such as P-waves, indicating natural atrial activity, and R-waves, indicating natural ventricular activity, said control means generating the timing signals needed to generate atrial and/or ventricular stimulation pulses on demand as needed in the absence of intrinsic P-waves and/or R-waves;
   stimulation pulse generating means coupled to said control means for generating said atrial and/or ventricular stimulation pulses in response to said timing signals;
   said control means including:
   PVARP generating means for generating a post ventricular atrial refractory period (PVARP) subsequent to the generation of each ventricular stimulation pulse or the sensing of an R-wave, said PVARP defining a time interval during which sensed atrial activity is not considered as a valid P-wave, said PVARP generating means generating at least a first PVARP and a second PVARP; and
   atrial pulse prevention means for preventing an atrial stimulation pulse from being generated that is in competition with atrial activity sensed during said PVARP.

2. The rate-responsive dual-chamber pacemaker, as set forth in claim 1, wherein said atrial pulse prevention means comprises:
   rate determining means for determining an intrinsic atrial rate;
   first comparison means for determining if said sensed intrinsic atrial rate is approaching a reference rate; and
   means responsive to said first comparison means for changing said first PVARP to a second PVARP, said second PVARP being different than said first PVARP.

3. The rate-responsive dual-chamber pacemaker, as set forth in claim 2, wherein said second PVARP is approximately 50 to 200 milliseconds shorter than said first PVARP.

4. The rate-responsive dual-chamber pacemaker, as set forth in claim 2, wherein said second PVARP changes as an inverse function of said physiological pacing rate.

5. The rate-responsive dual-chamber pacemaker, as set forth in claim 4, wherein said second PVARP changes as an inverse function of said physiological pacing rate only if said physiological pacing rate first increases.

6. A method of operating a rate-responsive, dual-chamber pacemaker so as to avoid generating atrial stimulation pulses that might compete with natural atrial activity, said pacemaker being programmed to operate in a DDDR mode of operation so as to provide stimulation pulses on demand at a rate determined by a physiological sensor, said method comprising the steps of:
   (a) sensing intrinsic P-waves;
   (b) determining if the sensed intrinsic P-waves are occurring at an intrinsic atrial rate that is at least as rapid as a reference rate;
   (c) in the event that a sensed intrinsic atrial rate is at least as rapid as said reference rate, as determined in step (b), changing a post ventricular atrial refractory period (PVARP) associated with said DDDR mode of operation, and
   (d) operating said pacemaker in said DDDR mode of operation with said changed PVARP for so long as the sensed intrinsic atrial rate is equal to or greater than said reference rate.

7. The method, as set forth in claim 6, further including the step of returning PVARP to its original value in the event that the sensed intrinsic atrial rate is not increasing and is less than said reference rate.

8. The method, as set forth in claim 7, wherein the step of changing said PVARP comprises shortening said PVARP.

9. The method, as set forth in claim 8, wherein the step of shortening said PVARP comprises shortening it a prescribed amount.

10. The method, as set forth in claim 8, wherein the step of shortening said PVARP comprises shortening it an amount that is inversely proportional to the rate determined by said physiological sensor.

* * * * *